United States Patent
Green

(10) Patent No.: US 9,597,213 B2
(45) Date of Patent: Mar. 21, 2017

(54) HANDLE MECHANISM FOR ACTUATING DELIVERY CATHETER

(71) Applicant: Abbott Cardiovascular Systems, Inc., Santa Clara, CA (US)

(72) Inventor: Michael Green, Pleasanton, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 153 days.

(21) Appl. No.: 14/620,472

(22) Filed: Feb. 12, 2015

(65) Prior Publication Data
US 2016/0235568 A1    Aug. 18, 2016

(51) Int. Cl.
A61F 2/95     (2013.01)
A61F 2/966    (2013.01)
A61F 2/82     (2013.01)

(52) U.S. Cl.
CPC ............... *A61F 2/95* (2013.01); *A61F 2/82* (2013.01); *A61F 2/966* (2013.01); *A61F 2002/9517* (2013.01)

(58) Field of Classification Search
CPC .... A61F 2002/9517; A61F 2/95; A61F 2/962; A61F 2/966; A61F 2/2436; A61F 2/2427
See application file for complete search history.

(56) References Cited

U.S. PATENT DOCUMENTS

| | | | | | |
|---|---|---|---|---|---|
| 5,944,727 | A | * | 8/1999 | Ahari | A61F 2/962 606/108 |
| 6,599,296 | B1 | * | 7/2003 | Gillick | A61B 17/3207 606/108 |
| 9,211,206 | B2 | * | 12/2015 | Pryor | A61F 2/97 |
| 2007/0244540 | A1 | * | 10/2007 | Pryor | A61F 2/95 623/1.11 |
| 2008/0208209 | A1 | * | 8/2008 | Fischer | A61F 2/966 606/108 |
| 2009/0105798 | A1 | * | 4/2009 | Koch | A61F 2/95 623/1.11 |
| 2009/0171433 | A1 | * | 7/2009 | Melsheimer | A61F 2/95 623/1.12 |
| 2012/0290066 | A1 | * | 11/2012 | Nabulsi | A61F 2/966 623/1.11 |

* cited by examiner

*Primary Examiner* — Christopher L Templeton
(74) *Attorney, Agent, or Firm* — David J. Pitman; Fulwider Patton LLP

(57) ABSTRACT

A handle for delivering, from a distal end of a catheter, a stent positioned within a sheath. The handle comprises an upper rack fixed to the handle and an upper distal block moveable along the upper rack and defining a pawl configured to permit only proximal movement in relation to the upper rack, further including an upper proximal block moveable along the upper rack and defining a pawl configured to permit only proximal movement in relation to the upper rack. The handle includes a lower rack configured to slide proximally and, alternatingly, distally in relation to the handle.

9 Claims, 7 Drawing Sheets

HANDLE MECHANISM FOR ACTUATING DELIVERY CATHETER

BACKGROUND

The present invention relates to systems for delivering a stent from a sheath positioned at the distal end of a delivery catheter. Specifically, the invention relates to systems configured to draw back a sheath surrounding a stent, while simultaneously pushing the stent distally from the interior of the sheath.

It is well known in the prior art to deliver self expanding stents from the distal end of a delivery catheter. Typically, a self-expanding stent is compressed into a first condition and inserted into a distal sheath that holds the stent in the first condition at the distal tip of the catheter. A stent engagement member, comprising an angled barb, may reside within an inner lumen of the stent prior to activation. Upon activation of the delivery system, and in a series of small repetitive actions, the sheath may be withdrawn, and subsequently the stent engagement member may push distally to engage with the stent and force the stent distally further outside of the sheath. It is typical that up to ten or twenty small movements involving sheath withdrawal and stent advancement may be undertaken before the stent is entirely deployed out of the sheath.

Problems arise in the prior art however. One problem is that the mechanical actions of withdrawing the sheath and pushing the stent do not typically take place simultaneously, but take place sequentially. This gives rise to a situation in which the sheath tends to frictionally drag the stent proximally when the sheath is withdrawn during an incremental movement, thereby displacing the stent on the catheter axis, and also compressing (i.e. shortening) the stent along its axis. Such compression may further result in the stent expanding radially by a small amount. This effect is problematic because the next incremental action, which is to push the stent distally, is complicated by the fact that the stent may have changed its location on the catheter and also may have changed its shape. In extreme situations, the mechanism designed to move the stent distally may be inoperable, because contact between the engagement member and the stent may have become disengaged. Another problem that arises in the prior art is that push and pull mechanisms designed to deploy self expanding stents from a sheath typically are not operably linked with each other. This has the result that a certain movement by the sheath does not correspond with a fixed amount of movement by the stent. Rather, the amount of movement of the push (stent) and pull (sheath) mechanisms are independent of each other and are determined by the physician user, who is often obliged to guess how much movement she has achieved with each mechanism after a certain amount of time, and how much further movement is needed.

Thus there is a need in the art for a delivery system that addresses the problems in the art. The present invention addresses these and other needs.

SUMMARY OF THE INVENTION

The present invention comprises a number of embodiments. In one embodiment, the invention is a handle for delivering, from a distal end of a catheter, a stent positioned within a sheath. The handle comprises an upper rack fixed to the handle. An upper distal block is provided, moveable along the upper rack and defining a pawl configured to permit only proximal movement in relation to the upper rack. An upper proximal block is provided, moveable along the upper rack and defining a pawl configured to permit only proximal movement in relation to the upper rack. A lower rack is provided, configured to slide proximally and, alternatingly, distally in relation to the handle. A lower distal block is provided, moveable along the lower rack and defining a pawl configured to permit only proximal movement in relation to the lower rack. A lower proximal block is provided, moveable along the lower rack and defining a pawl configured to permit only proximal movement in relation to the lower rack.

Under this configuration, the upper distal block is operably connected to a proximal end of a sheath actuator, a distal end of the sheath actuator being operably connected to a sheath, and further, the lower proximal block is operably connected to a proximal end of a stent actuator, a distal end of the stent actuator being operably connected to a stent engagement member.

In some embodiments, the handle further includes a beam, an upper distal link connected at a first end to the upper distal block and at a second end to the beam, an upper proximal link connected at a first end to the upper proximal block and at a second end to the beam, a lower distal link connected at a first end to the lower distal block and at a second end to the beam, and a lower proximal link connected at a first end to the lower proximal block and at a second end to the beam. In some embodiments, the handle includes a means for executing an action in which distal movement of the lower rack causes the upper distal block to move proximally in relation to the upper rack, and the lower distal block to move proximally in relation to the lower rack, and, in which proximal movement of the lower rack causes the upper proximal block to move proximally in relation to the upper rack, and the lower proximal block to move proximally in relation to the lower rack. In some embodiments, the handle includes a trigger pivotingly connected to the handle and in communication with the lower rack, whereby activation of the trigger causes distal movement of the lower rack. In some embodiments, the handle includes a spring connected between the handle and the lower rack and configured to bias the lower rack in a proximal direction. In further embodiments, the sheath actuator is an elongate tube, and the stent actuator is an elongate cylinder, which may take the form of a rod in some embodiments, or as a tube in other embodiments. In some of these embodiments, the sheath actuator is an elongate tube and the stent actuator is an elongate cylinder sized to slide within a lumen of the sheath actuator. In other embodiments, the handle includes a means for preventing the upper distal block from moving proximally when the lower proximal block is moving proximally. In yet other embodiments, the handle includes a means for preventing the lower proximal block from moving proximally in relation to the lower rack when the lower rack is moving distally in relation to the handle.

In another embodiment, the invention is a method for deploying, from a distal end of a catheter, a stent positioned within a sheath. The method comprises the steps of moving a rack distally within a handle of the catheter. Simultaneously, the stent is moved distally in relation to the catheter. Further simultaneously, the sheath is moved proximally in relation to the catheter.

In some embodiments, the method includes following the foregoing steps by the steps of moving the rack proximally within the handle, and, simultaneously, moving a stent engagement member proximally in relation to the catheter. Other embodiments include the step of, simultaneously with moving the rack proximally, maintaining the sheath stationary in relation to the catheter.

Yet further embodiments include the step of, simultaneously with moving the rack proximally, maintaining the stent stationary in relation to the catheter. Under these actions, moving the rack proximally includes releasing a trigger pivotably fixed to the handle. In some embodiments, moving the rack proximally includes moving the rack under bias of a spring; and further, moving the stent distally and simultaneously moving the sheath proximally includes moving the stent distally a first distance and moving the sheath proximally a second distance, wherein the first distance is greater than the second distance. Optionally, the step of moving a rack distally includes pulling a trigger pivotably fixed to the handle.

These and other advantages will appear from a reading of the detailed description of the embodiments in conjunction with the figures.

DETAILED DESCRIPTION OF EMBODIMENTS

Figure 4:
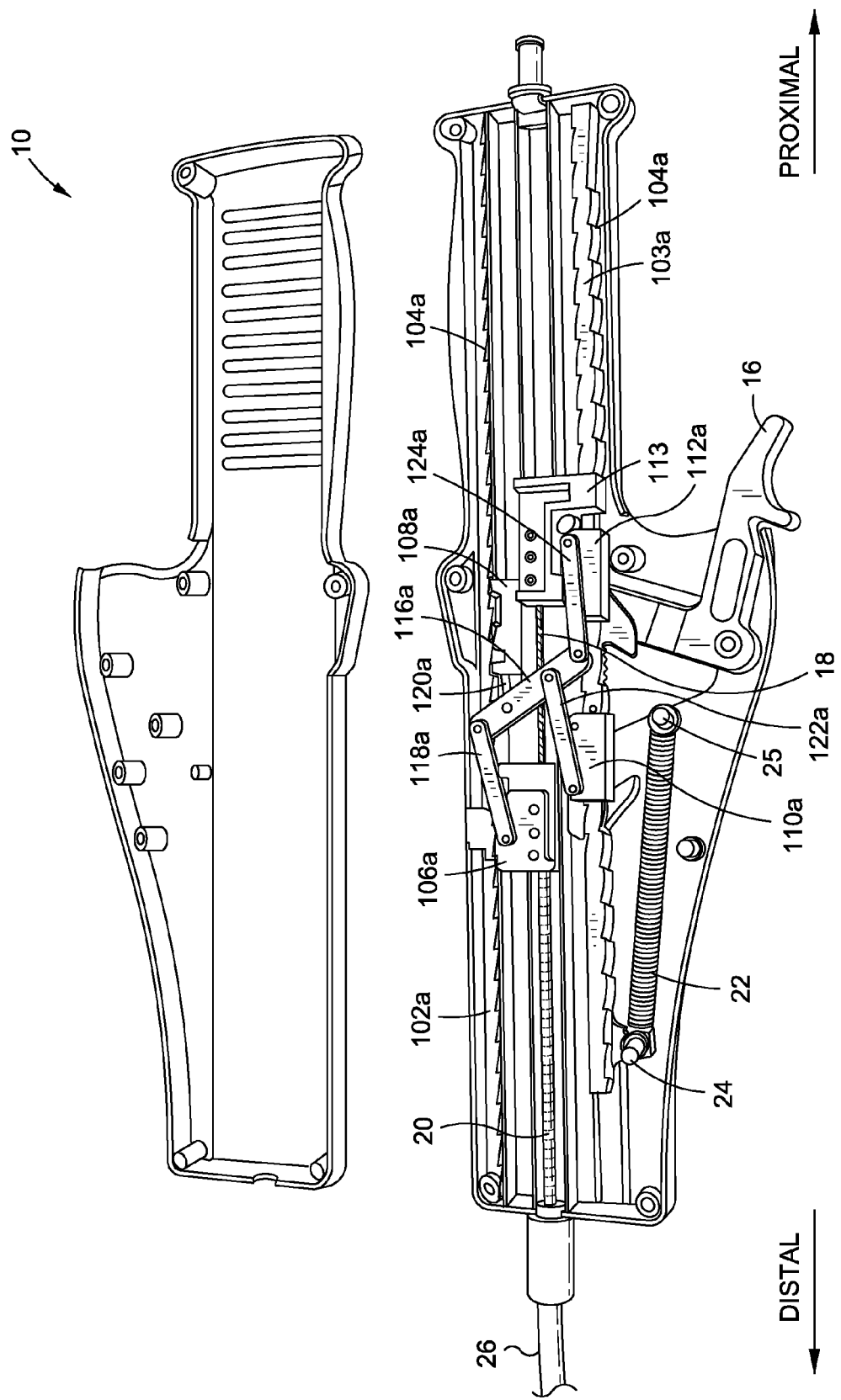
FIG. 4. is a side perspective view of a handle located at a proximal end of a catheter, in opened up condition to expose components, showing features of the invention.
Figure 5:
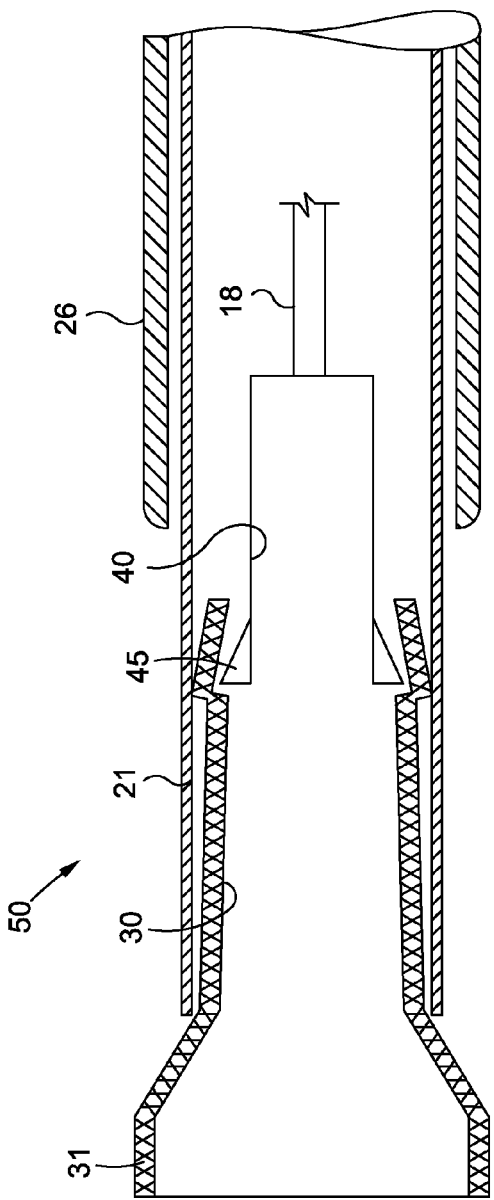
FIG. 5. is a schematic sectional view of a distal end of a catheter, in which a stent and sheath are shown that are deployed by the handle shown in FIG. 4.
Figure 6:
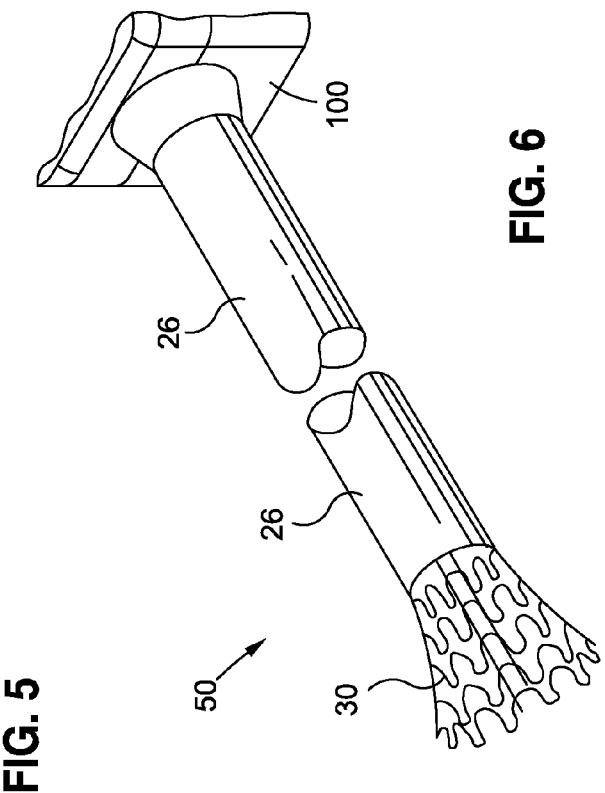
FIG. 6 is a perspective view in partial cutaway, showing the distal catheter end which is seen in FIG. 5.

The present description is of a catheter related system having features of the invention. In one embodiment, the system includes a handle 10 containing a mechanism and which is connected to a catheter body 26 such as seen in FIGS. 4-6. The catheter body 26 is designed to be inserted into the vasculature of a patient. At the distal tip 50 of the catheter body 26, a stent 30 is located. FIG. 5. For insertion into the patient, the stent is compressed into a first condition, and is confined in a sheath 21. During deployment of the stent 30, the sheath 21 is slowly withdrawn proximally, and the stent is simultaneously advanced distally, so that the stent is allowed to expand at an optimal rate. The present invention, as described in the detail description below, will enable such stent deployment in a highly advantageous manner.

The handle 10 includes in its interior a mechanism which is specially configured to provide sheath retraction, and, simultaneously, stent advancement at advantageous relative speeds and amplitudes.

Figure 1:
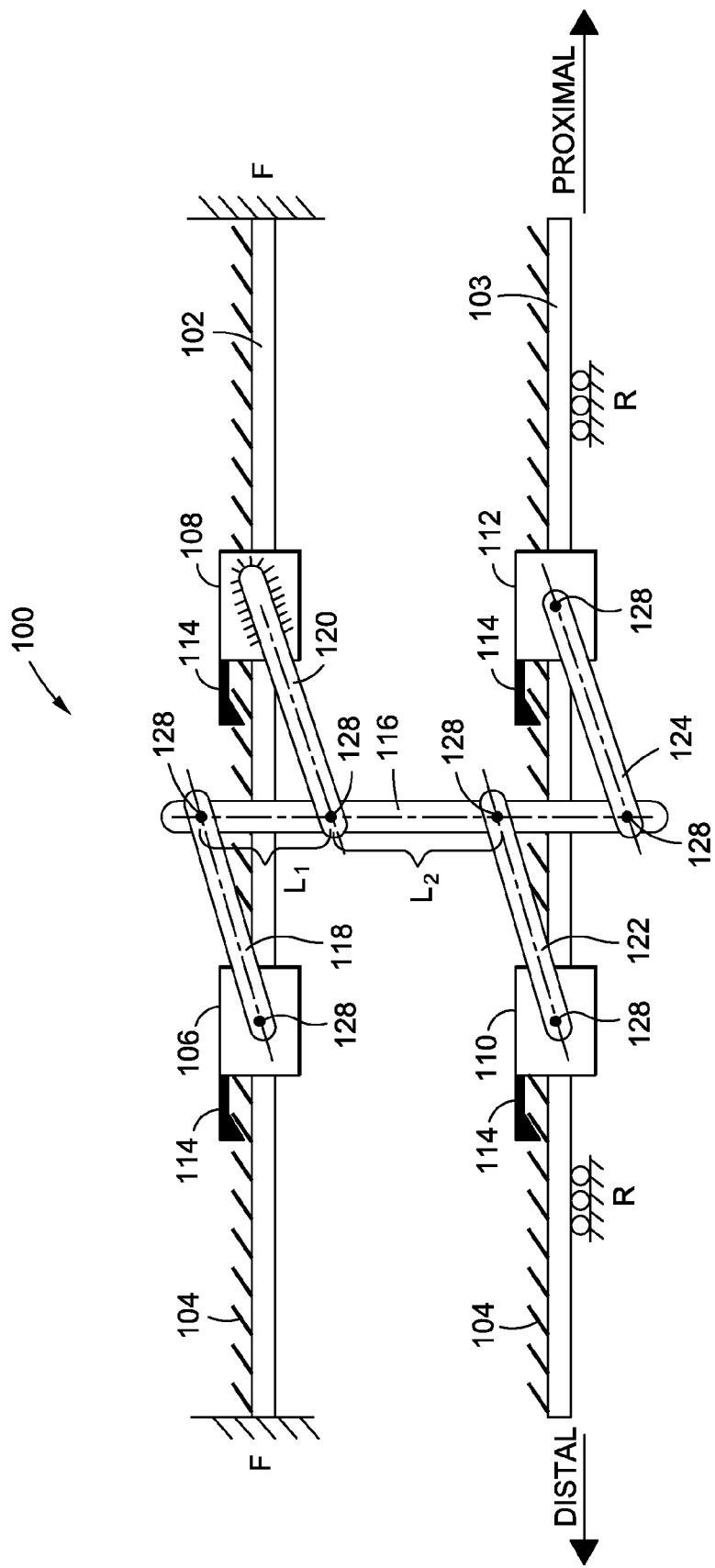
FIG. 1 is a schematic drawing of a mechanism of a kind that is used in an embodiment of the invention, shown in a first condition.
Figure 2:
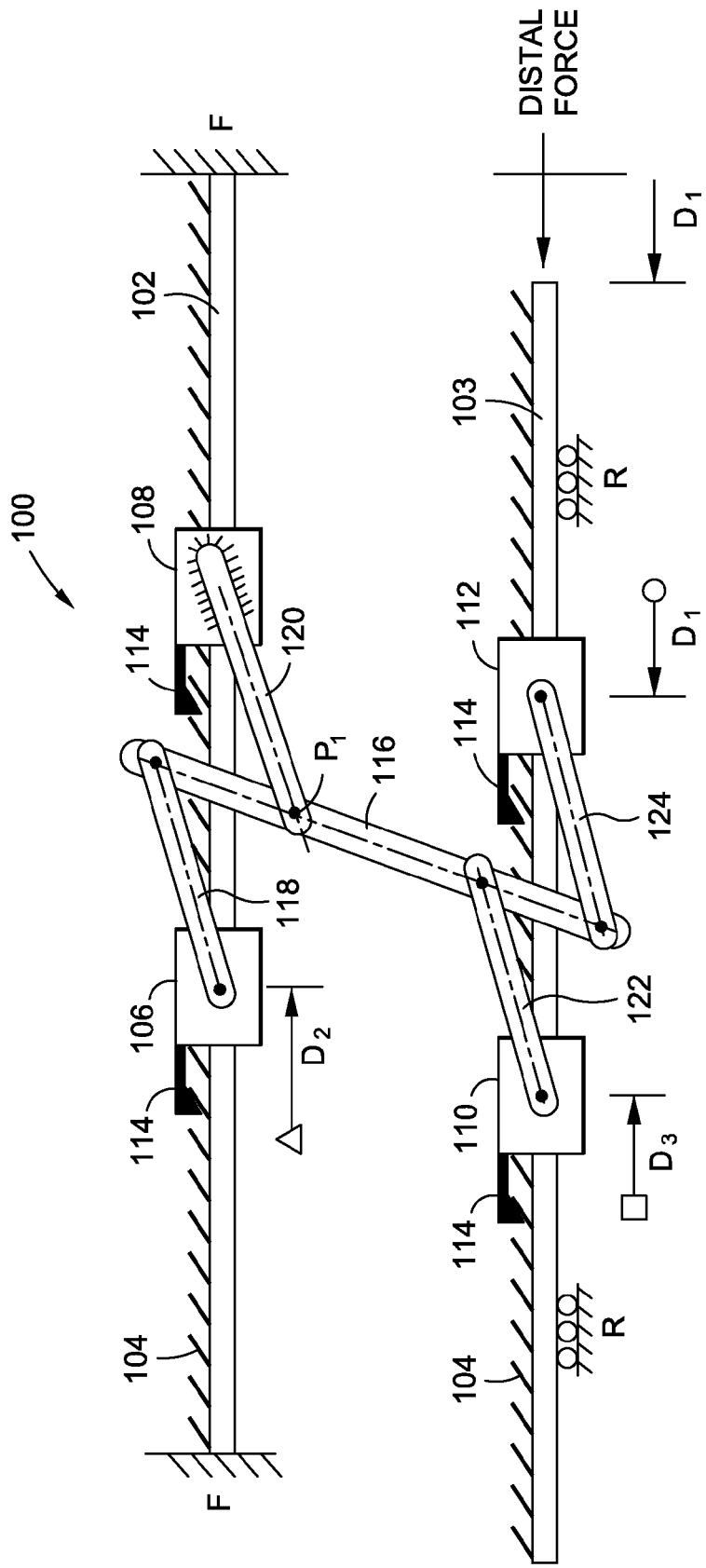
FIG. 2 is a schematic drawing of a mechanism of a kind that is used in an embodiment of the invention, shown in a second condition.
Figure 3:
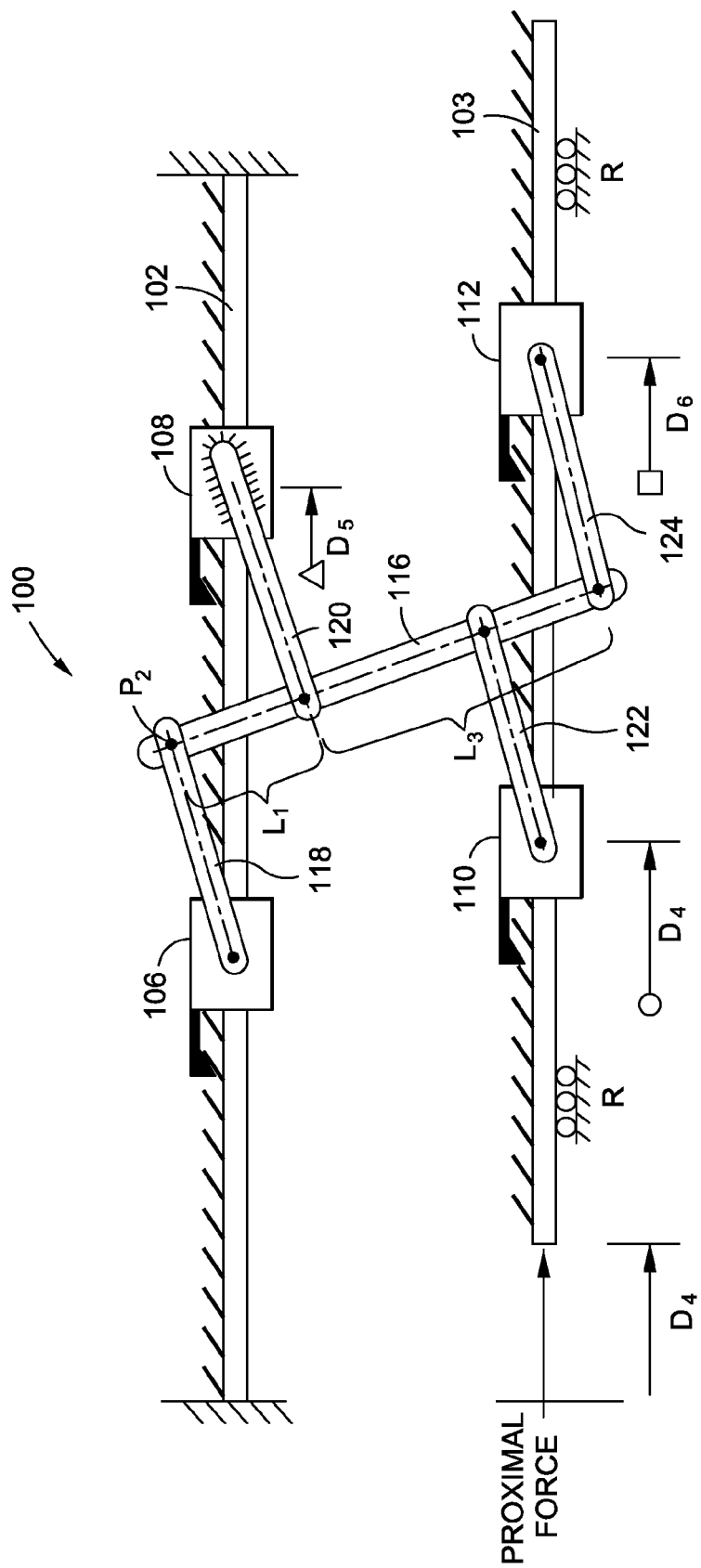
FIG. 3 is a schematic drawing of a mechanism of a kind that is used in an embodiment of the invention, shown in a third condition.

Turning now to a description of general mechanical principles under which the present invention operates, reference is initially made to FIGS. 1-3. In each figure the structure of a differential advancement mechanism 100 is shown schematically, in different stages of operation. In each figure the mechanism includes the following elements: An upper slide rack 102 includes an elongate rack configured to guide two slideable blocks along the rack. A lower slide rack 103 is structurally similar to the upper slide rack. However, the upper slide rack 102 is fixed (onto the handle of the invention which is not shown in FIGS. 1-3), and this feature is schematically indicated in FIGS. 1-3 by fixed ends "F". The lower slide rack 103 is configured to move linearly forwards and backwards (distally and proximally) within the handle, and this feature is schematically indicated by rollers "R" shown supporting the lower slide rack. Each rack 102, 103 includes ratchet teeth 104 angled to prevent movement distally. (The term "rack" may be understood herein to be equivalent to "ratchet" —meaning an elongate element with a plurality of teeth angled in only one direction.) Two blocks are attached to the upper rack, an upper distal block 106, and an upper proximal block 108. Each upper block includes a pawl 114 angled so that, in cooperation with the teeth 104 of the upper rack, the upper blocks can only move proximally in relation to the upper rack. Further, two blocks are attached to the lower rack, a lower distal block 110, and a lower proximal block 112. Each lower block includes a pawl 114 angled so that, in cooperation with the teeth 104 of the lower rack, the lower blocks can only move proximally in relation to the lower rack.

Connecting the four blocks 106, 108, 110, 112 in relation to each other are a beam connected to a series of links. A beam 116 extends substantially vertically and is positioned between the two distal blocks on the one hand, and the two proximal blocks on the other. An upper distal link 118 connects the upper distal block 106 to the beam, by pin connections 128 at each end of the link. An upper proximal link 120 connects the upper proximal block 108 to the beam, with a pin connection between the links and beam but a fixed connection between upper proximal link 120 and upper proximal block 108. This fixed connection is necessary to avoid too many degrees of freedom in the mechanism. A lower distal link 122 connects the lower distal block 110 to the beam 116, by pin connections 128 at each end of the link. A lower proximal link connects the lower proximal block 112 to the beam 116, by pin connections 128 at each end of the link. In this embodiment, the proximal ends of the distal links 118, 122 are connected at points on the beam 116 that are above the distal ends of the proximal links 120, 124, as may be envisaged by reference to FIGS. 1-3.

The mechanism 100 is shown in a "starting" position in FIG. 1, before any motion of the mechanism has begun. In operation of the mechanism, the lower rack 103 is moved distally by a distance shown as D1 in FIG. 2. (This movement may correspond with the movement of a trigger on a handle of the invention, as will be explained below.) It will be appreciated that distal movement of the lower rack 103 causes the beam 116 to tilt in such a way that, in combination with the geometry of the other four links 118, 120, 122, 124 of the mechanism, the two upper block 106, 108 are urged to move towards each other, and the two lower blocks 110, 112 are also urged to move towards each other. However, due to the configuration of the ratchet and pawl system on each of the blocks, the proximal blocks 108 and 112 are unable to move distally in relation to their neighboring distal block, but are locked in a stationary position in relation to their respective racks 102, 103. It will be appreciated that, accordingly, each distal block 106, 110 will be moved proximally in relation to their respective racks because their pawls permit such movement. Thus, as schematically shown in FIG. 2, a distal movement of D1 imparted to the lower rack 103 will impart a proximal movement of D2 by upper distal block 106 in relation to its respective rack 102, and proximal movement D3 by lower distal block 110 in relation to rack 103. However, because block 108 does not move, the effective pivot point for the beam 116 under this action is the distal end of the upper proximal link 120, marked as P1 in FIG. 2. One of ordinary skill will appreciate that due to the different lengths of the lever arms on either side of pivot point P1, the proximal movement D2 of upper distal block 106 in relation to the proximal movement D3 of lower distal block 110 will be in proportion to the lever arms L1 and L2 as marked in FIG. 1. Additionally, it will be appreciated that block 112, being locked onto the moving lower rack 103 will also move distally by a distance D1 in relation to the handle as marked in FIG. 2. For clarity, block distances that are moved in relation to the handle but do not move in relation to moving rack 103, are marked with a circle on the tail of the distance arrow; distances that are moved in relation to the lower rack 103 (which is itself moving) are marked with a square on the tail of the arrow; distances that are moved on stationary rack 102 are marked with a triangle on the tail of the arrow.

In further operation of the mechanism, the lower rack 10 may be moved proximally by a distance shown as D4 in FIG. 3. (This movement may correspond with the urging of a return spring in the handle of the invention, as will be explained below.) It will be appreciated that movement of the lower rack 103 proximally causes the beam 116 to tilt in such a way that, in combination with the geometry of the other four links 118, 120, 122, 124 of the mechanism, the two upper block 106, 108 are urged to move apart from each other, and the two lower blocks 110, 112 are also urged to move apart from each other. However, due to the configuration of the ratchet and pawl system on each of the blocks, the distal blocks 106 and 110 are unable to move proximally toward its neighboring block, but are locked in a stationary position in relation to their respective racks 102, 103. It will be appreciated that, accordingly, each proximal block 108, 112 will be urged to move distally in relation to their respective racks because the ratchets and pawls permit such movement. Thus, as schematically shown in FIG. 3, a proximal movement of D4 imparted to the lower rack 103 will impart a proximal movement of D5 by upper proximal block 108 in relation to respective rack, and proximal movement D6 by lower distal block 110. However, because block 106 does not move, the effective pivot point for the beam 116 under this action is the proximal end of the upper distal link 118, marked as P2 in FIG. 3. Additionally, it will be appreciated that block 110, being locked onto the lower rack 103 will also move proximally by a distance D4 in relation to the handle. One of ordinary skill will appreciate that due to the different lengths of the lever arms on the beam 116 below pivot point P2, the proximal movement of upper proximal block 108 in relation to the proximal movement of lower proximal block 112 will be in proportion to the lever arms (L1) and (L1 plus L3) as indicated in FIG. 3.

It will be readily understood from the foregoing description that an oscillating proximal/distal movement of the lower rack 103 will cause all four blocks 106, 108, 110, 112 to gradually move proximally in relation to their respective racks 102, 103. First, the two distal blocks 106, 110 are moved proximally (D2 and D3 as in FIG. 2), followed by an action in which the proximal blocks 108, 112 are moved proximally (D5 and D6 as in FIG. 3). Furthermore, due to the differing lengths of the lever arms on beam 116, the upper blocks will move proximally more slowly than the lower blocks.

Having established how the mechanism 100 works, it is in some embodiments an objective to harness the movement of the blocks of the mechanism in relation to a handle for stent deployment in order to provide for two actions simultaneously namely, (a) the slow but steady retraction (proximally) of a sheath at a distal end of a catheter and (b) the oscillating motion of a stent engagement member which is barbed so as to provide only distal movement of a stent.

In order to accomplish this objective, a mechanism of the kind described above is installed in a handle 10 of a stent delivery catheter, as seen in FIG. 4, where counterpart elements are given the same identifying numeral as those elements identified in FIGS. 1-3, but are marked with a suffix "a" to indicate that an element in the handle 10 is being referenced. As may be seen in FIG. 4, an upper first rack 102a is formed with teeth 104a as part of the handle interior wall. Similarly, a lower second rack 103a is formed with teeth 104a as a sepate element, slideable back and forth (proximally and distally) on runners inside the handle. An upper distal block 106a rides on the upper first rack, and an upper proximal block 108a rides on the upper rack. A pawl (not visible in FIG. 4) is provided on each block 106a and 108a. A lower distal block 110a rides on the lower second rack, and a lower proximal block 112a rides on the lower rack. A pawl (not visible in FIG. 4) is provided on each block 110a and 112a. A beam 116a is provided, and an upper distal link 118a, upper proximal link 120a, a lower distal link 122a, and a lower proximal link 124a are provided, and each is attached to a related block by pin connection according to a similar geometry as that described for mechanism 100 in FIGS. 1-3. Notably, the upper proximal link 120a in this embodiment is not pinned, but rotationally fixed, to the upper proximal block 108a, as is the equivalent case in mechanism 100.

In addition to element equivalents in mechanism 100, the handle 10 includes a pivotable trigger 16 which is configured in a known manner in relation to the lower rack 103a so that movement of the trigger upwards engages teeth on the trigger (not seen in FIG. 4) with teeth (also not seen in FIG. 4) on a lateral side of the lower rack 103a, and this engagement facilitates the lower rack 103a to move distally upon pulling the trigger. A further element in the handle is a helical spring 22 which extends substantially parallel with the lower rack 103a. At a proximal end the spring is connected to a pin 25 that is molded into the handle, and at the distal end the spring is connected to a pin 24 that is molded to form part of the lower rack 103a. Thus, movement of the rack 103a distally (as may be envisaged with respect to FIG. 4) will cause the spring to stretch and to thus bias the lower rack 103a proximally. Thus, if the trigger is pulled upwardly, the lower rack 103a will move distally, but when the trigger is released, the spring will pull the lower rack 103a proximally, which action will pull the trigger downwards to its start position.

Turning briefly to a description of FIG. 5, this figure shows, schematically in section, the distal end portion 50 of the stent delivering catheter to which the handle 10 is connected. It shows the relationship between a stent engaging member 45, a sheath 21, and a stent actuator 18 which may be connected to biasing elements 40 that provide the stent engaging member 45 with a radially outward bias. A self expanding stent 30 is confined within the sheath 21. A stent engaging member 45 (which may comprise a pair of opposite stent engaging members 45) is positioned within the internal lumen of the stent 30. The stent engaging members comprise sharp distally pointing hooks or barbs, and are mounted on spring loaded arms or biasing elements 40 that are shaped to urge the stent engaging members radially outwardly, so as to engage with the fabric of the self expanding stent 30. Distal movement of the stent engaging members 45 will cause the stent engaging members to lodge in the fabric of the stent, and will move the stent distally, as may be envisaged with reference to FIG. 5, which shows the sharp points of the stent engaging member 45 partially distorting the proximal fabric of the stent 30. As the stent is forced distally to emerge from the sheath 21, the distal tip 31 of the stent expands radially outwardly, as seen in FIG. 5. The stent-engaging member 45 of FIG. 5 may be similar to that exemplified and described in commonly owned application Ser. No. 13/118,325 (incorporated by reference), and as exemplified in FIG. 8 in that application. A catheter cover 26 may be configured to enclose the stent and its delivery mechanism during delivery of the catheter to the desired location in the vasculature of the patient.

Returning to FIG. 4 then, additional structure is described. Activation elements for a stent and a sheath are connected to the blocks as follows. A sheath actuator 20 has the form of a thin hollow tube, as seen in FIG. 4. At a distal end the sheath actuator 20 is connected to the upper distal block 106*a*, so that movement of the distal upper block in relation to the handle is followed by identical movement of the sheath actuator 20 in relation to the catheter.

The sheath actuator 20 extends all the way from its proximal end at block 106*a*, out of the handle 10, and into a catheter cover 26 which is the outermost member of the catheter portion that is configured to be inserted into a patient's vasculature. At a distal end, the sheath actuator 20 may be operably connected (connection not shown) to a sheath 21 configured to confine the stent 30, as may be seen in FIG. 5. It will be appreciated that, due to the distal block 106*a* and the sheath 21 being operably connected, movement of the upper distal block 106*a* in relation to the handle 10 will be followed by equal movement of the sheath 21 in relation to the catheter. As used herein, an "operable" connection between two elements is used to indicate a connection that is not necessarily directly between the two elements, but may include a third element between the two elements.

Still referring to FIG. 4, another activation element found in the handle 10 is the stent actuator 18, which may take the form of a thin cylinder sized to slide within the hollow sheath actuator 20. In one embodiment, the cylinder may be a solid rod. In another embodiment, the cylinder may take the form of a thin hollow tube sized to slide within the hollow sheath, and the bore of the hollow tube may be sized to receive a guidewire. A proximal end of the stent actuator 18 is attached to the lower proximal block 112*a* (or, as shown in FIG. 4, to a shuttle 113 that is configured to act in unison with block 112*a* as is more fully described below), and extends distally through upper distal block 106*a* before entering a lumen of the sheath actuator 20. A distal end of the stent actuator may be connected (as seen in FIG. 5) with the biasing element 40 connected to stent engaging member 45 as described above. It will be appreciated that movement of the lower proximal block 112*a* in relation to the handle 10, will result in equal following movement of the stent engagement member 45 in relation to the catheter.

In operation of the structure thus described, a physician user may start by inserting the distal end 50 of the catheter into the vasculature of a patient. Once she is confident that the undeployed stent 30 is located at the correct position within the vasculature using conventional means, she takes steps to deploy the stent 30. Deployment of the stent will involve slowly withdrawing the sheath 21 that surrounds the stent 30 thus allowing the stent to expand from its compressed condition to an expanded condition. It also involves pushing the stent 30 distally using the stent engaging members 45 in order to prevent the sheath 21 from slowly compressing the stent axially by frictional drag, and also to prevent the sheath 20 from frictionally dragging the position of the entire stent proximally. These latter two phenomena, axial compression and proximal movement of the stent are problems in the art, and there is a need for stent delivery catheters that can address these problems.

To accomplish the above action following the mechanical principles outlined above with respect to the mechanism 100, the user pulls the trigger 16 upwards, thereby advancing the lower rack 103*a* distally by an amount D1 as exemplified in FIG. 2. As further explained with respect to FIG. 2, this action will cause the upper distal block 106*a* to move proximally (by distance D2 as in FIG. 2) and thereby to move the sheath actuator 20 proximally by the same amount. This movement in turn causes the sheath 21 at the distal end 50 of the catheter to move proximally by the same distance D2, thereby slowly revealing the stent 30, which expands to a larger diameter at its tip 31 which in turn is placed in contact with the vasculature wall (vascular wall not shown in the figures). At the same time as the lower rack 103*a* moves distally by distance D1, the lower proximal block 112*a* also moves distally by D1 (as a consequence of being locked onto the moving lower rack 103*a*). The stent actuator 18 and hence the stent engagement member 45, move distally by the same amount D1. This distal movement of the stent engagement member 45 forces the member 45 to engage with the fabric of the compressed stent 30 as seen in FIG. 5, and to force the stent distally out of the sheath.

Next, the user releases the trigger 16, and the spring 22 biases the lower rack 103*a* proximally by a distance D4 as exemplified in FIG. 3. This causes the lower distal block 112 to move proximally by distance D6, and consequently, to move the stent actuator 18 and coupled engagement member 45 distally by the same amount. This action withdraws the stent engagement member 45 towards the proximal end of the stent 30, and positions it for the next distal action when the trigger is pulled again. At the same time as engagement member 45 is withdrawn proximally, upper distal block 106*a* remains stationary on the upper rack 102*a*, and hence the sheath actuator 20 and coupled sheath 21 remain motionless while the engagement member 45 is being repositioned for the next distal push.

It will be appreciated by one of ordinary skill that a series of trigger pulls repeats the actions described above, but that each trigger pull sequence causes the four blocks to move collectively toward the back (proximal end) of the handle. Thus, the sheath 21, in a series of uni-directional movements (proximally), is retracted proximally to expose the entire stent. Further, the angled stent engagement member 45 in a series of bidirectional actions (proximal and distal) forces the stent 30 out of the sheath 21. Of course, the distal most reach of the engagement member 45 in each stroke slowly retreats proximally as the lower distal block 112*a* moves proximally along the lower rack 103*a* during oscillation of the trigger. But this feature advantageously allows the distal most reach of the engagement member 45 to retreat in conjunction with the distal edge of the sheath 21, so that each distal "push" of the engagement member 45 ends at a point adjacent to the distal edge of the sheath.

Thus, the invention provides a novel and useful system for deploying a self expanding stent from a delivery catheter, in which problems in the art, and other problems, are addressed.

In a further embodiment of the invention, further features may be included to the foregoing embodiments to ensure faithful operation of the mechanism according to the principles stated above. In this regard, it may be noted that two problems may manifest themselves during operation of the foregoing embodiment.

The first problem is that, if the ratchet and pawl systems present on the two lower blocks 110a and 112a are too "efficient"—meaning that they provide very low frictional resistance when the lower second rack 103 moves distally in relation to these blocks—then the lower rack moving distally may tend to simply slide right past both blocks 110a, 112a without imparting any movement to either block or the beam 116a, thereby failing to activate the mechanism.

The second problem is that, when the stent actuator 18 is drawn proximally by the lower proximal block 112a, (as equivalently shown in the action of FIG. 3) the stent actuator 18 may tend to frictionally drag the sheath actuator 20 proximally due to the fact that the sheath actuator closely surrounds the stent actuator. The sheath actuator 20 is connected to upper distal block 106a which, while fixed against distal movement, is not fixed against proximal movement. Thus, proximal drag on the sheath actuator 20 by the stent actuator 18 may cause the upper distal block 106b to move proximally during this action, and therefore may cause the mechanism not to function with the desired movement sequence. Both of these, if they occur, would be disadvantageous tendencies as they may interfere with the precise functioning of the mechanism.

To the extent that these tendencies may occur, a solution is presented herein below with reference to FIGS. 7A and 7B. In these figures, the various elements that are also found in FIG. 4 are given the same numerals but with the suffix "b" to indicate that an embodiment is shown with some modified elements. It should be understood however, that the invention is described herein so that elements with reference numeral with the "a" and "b" suffix play a similar role to each other and to the elements of similar reference numeral shown without any suffix, and that this methodology of description is followed to make it easier to read the specification and understand the operation of the embodiments. FIG. 7B is a view of the same handle as in FIG. 7A, but element 107 (ratchet 107) is removed in FIG. 7B in order to provide a clearer view of the remaining elements.

Figure 7A:
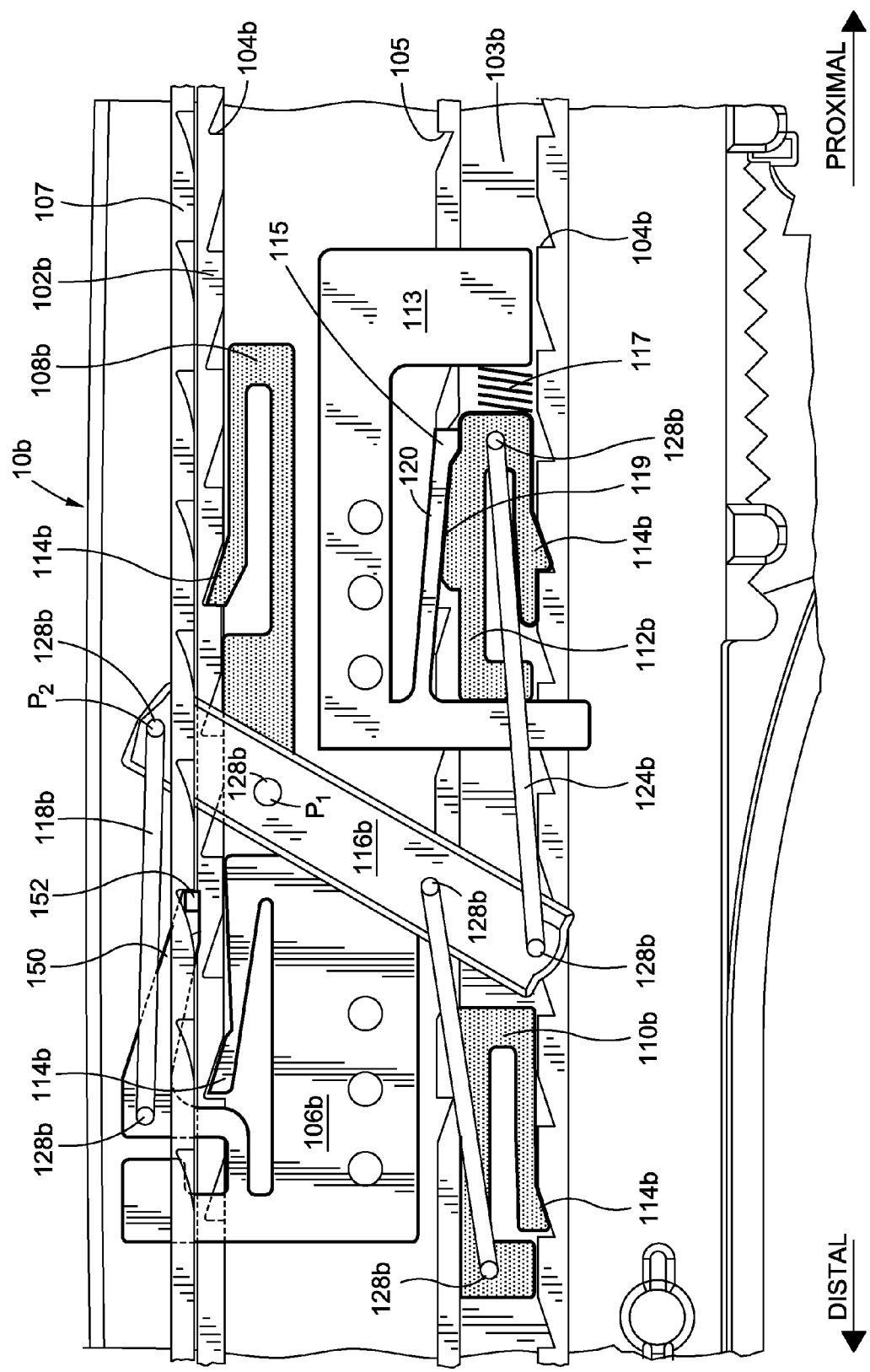
FIG. 7A is a side elevational view of a handle, in opened up condition to expose components, showing features of a further embodiment of the invention.
Figure 7B:
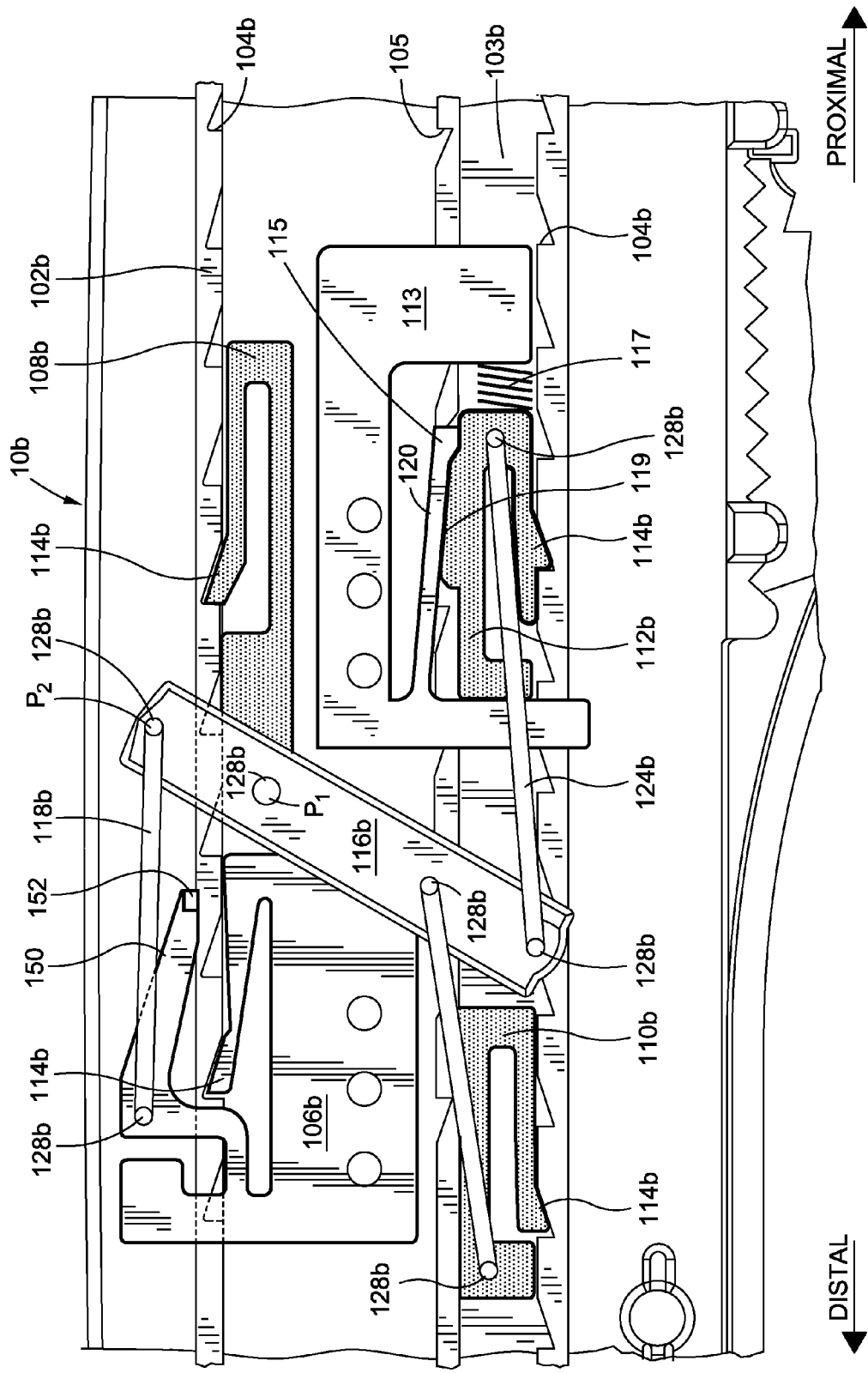
FIG. 7B is a side elevational view of the handle shown in FIG. 7A, with a component removed to give clarity of view of the remaining components.

With regard to the first problem stated above, and as exemplified in FIGS. 7A and 7B, lower proximal block 112b is provided and has an equivalent function to block 112. Rail 103b in this embodiment includes teeth 104b, operating in combination with pawl 114b on block 112b, to prevent distal movement of the block 112b and allow movement of block 112b only proximally in relation to the lower rack. However, in this embodiment, lower proximal block 112b is surrounded by an inverted U shaped shuttle 113 that rides along rail 103b in conjunction with the movement of block 112b. Downward facing arms of the shuttle are separated by a distance that is sufficient to accommodate the lower proximal block 112b and also a spring 117 positioned to bias the block 112b distally in relation to the proximal arm of the shuttle 113. The lower proximal block 112b defines a ramp 119 on its upper surface that slopes upwardly in a distal direction. The shuttle 113 includes a cantilevered arm 120 that extends slidingly across the ramp 119. The proximal tip of the arm 120 ends in a pawl 115 which is configured to act in conjunction with an additional linear toothed rack or ratchet 105 attached to the lower rack 103b and configured to move in conjunction with the lower rack. The rack 105 is configured to permit movement of the pawl 115 only in a distal direction in relation to the rack 103b.

In operation, this embodiment will demonstrate the following capabilities. When the lower rack 103b is pushed distally in relation to the handle 10b, the pawl 115 will engage with the teeth of ratchet 105, thus preventing the rack 103b from sliding distally past block 112b because block 112b is captured within the arms of the shuttle 113. Thus, distal movement of the combined racks 103b and 105 necessarily causes block 112b to move distally, and this movement necessarily forces the beam 116b to adopt an angled position similar that shown in FIG. 2, thereby preventing the first problem stated above from occuring. However, when the lower rack 103b is pulled proximally in relation to the handle, the mechanism will tend to adopt the equivalent position as exemplified in FIG. 3. This action causes the link 124b to push proximally on lower proximal block 112b. A small proximal movement by block 112b in relation to the shuttle 113 is permitted by the fact that the spring 117 will be caused to compress to some degree. This small movement of the block 112b in relation to the shuttle causes the ramp 119 to move proximally under the cantilever arm 120, thereby lifting the arm. This lifting in turn disengages pawl 115 from ratchet 105, and the block 112b (in combination with the shuttle 113) is free to move proximally in relation to the lower rack. At the end of proximal travel by the block 112b, the spring 117 biases the block 112b distally in relation to the shuttle 113, and the pawl 115 is lowered by its movement in relation to the ramp 119. This action re-engages the pawl 115 with the ratchet 105, and the mechanism is ready for the next distal movement of the rack 103b to provide the oscillating motion described above with reference to FIGS. 1-3. These features solve the first problem stated above.

With regard to the second problem stated above, and as exemplified in FIGS. 7A and 7B, an upper distal block 106b is provided. In this embodiment, however, block 106b is configured to include a bent cantilevered arm 150 extending initially upwards, and is then bent to extend proximally. At the tip of the arm 150 is a pawl 152 which is configured to normally engage with an additional ratchet 107 that may be formed in an opposing wall of the handle 10b. (The term "normally" signifies that, absent any unbalanced force on the cantilever 150, the pawl will engage with the ratchet 107). The additional ratchet 107 as seen in FIG. 7A lies in a plane closer to the viewer than all the other elements in FIG. 7A, and its teeth are positioned above the pawl 152. The ratchet 107 is configured with teeth so that, in conjunction with the pawl 152, the upper distal block 106b cannot move proximally when pawl 152 is engaged with ratchet 107. Thus, when the lower rack 103b is moved proximally (the condition under which the second problem occurs), the upper distal link 118b is placed in compression as may be understood with reference to FIG. 3. This compressive force in the link will cause the cantilever 150 to bend upwards, and will thereby force engagement of the pawl 152 in the teeth of rack 107. Thus, under this condition, the upper distal block 106b will be prevented from moving proximally. This prevention has the beneficial result that the sheath actuator 20 (attached to block 106b) cannot be moved proximally by frictional drag caused by the stent actuator 18 when the stent actuator is moved proximally. Conversely, when the lower rack 103b is moved distally, the upper distal link 118b is placed in tension, as may be understood with reference to FIG. 2. This force in the link will cause the cantilever 150 to bend downwards, and will thereby disengage the pawl 152 from the teeth of rack 107. Thus, under this condition, the upper distal block 106b is free to move proximally in accordance with the principles of the mechanism.

Thus, it will be appreciated by one of ordinary skill in the art that the structure described above enables a system that, in one embodiment, carries out a method for deploying, from a distal end 50 of a catheter, a stent 30 positioned within a sheath 21. The method includes moving a rack 103b distally within a handle 10b of the catheter. Simultaneously with this action, the method includes moving the stent distally in relation to the catheter. Further simultaneously, the sheath is moved proximally in relation to the catheter. This is inherently achieved by the mechanism which has been described in relation to FIGS. 1-4 and 7 in which distal movement of the lower rack 103a will (a) cause the upper distal block 106a to move proximally, along with the sheath actuator 20; and simultaneously, (b) cause the lower proximal block to move distally, along with the stent actuator 18 (and hence the stent 30), as understood with reference to FIG. 2. The method may also include, following the foregoing steps, moving the rack proximally within the handle and simultaneously, moving a stent engagement member proximally in relation to the catheter. These latter actions arise due to the spring return action of the lower rack 103a, which moves the lower rack proximally, and also moves the lower proximal block 112a proximally, along with the attached stent actuator, and hence the stent engagement member 45. The method may further include the step of, simultaneously with moving the rack proximally, maintaining the sheath stationary in relation to the catheter. This result arises from the action of the block 106b with its cantilevered arm 150, and the engagement of pawl 152 with the teeth of rack 107. In other words, when the lower rack is pulled proximally along with the stent actuator 118, the sheath actuator is locked against proximal movement by the pawl 152, and this maintains the sheath stationary in relation to the catheter. The method may also include the further step of, simultaneously with moving the rack proximally, maintaining the stent stationary in relation to the catheter. This action arises from the fact that when the stent actuator 118 moves the stent engagement member 45 proximally, the stationary sheath 21 frictionally holds the stent stationary in relation to the catheter. In some embodiments, moving the rack proximally includes releasing a trigger pivotably fixed to the handle, and this includes moving the rack proximally under bias of the spring 22. In another aspect, moving the stent distally and simultaneously moving the sheath proximally (as described above) includes moving the stent distally a first distance and moving the sheath proximally a second distance, wherein the first distance is greater than the second distance. This result follows from the fact that the lever arms moving the lower proximal block (along with the stent actuator 118) and the upper distal block (along with the sheath actuator 120) are different lengths, as described above.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. For example, the words "upper" and "lower" are used to clearly distinguish between two elements, but it is within the scope of the invention to invert upper with lower without changing the invention. The terms "proximal" however, refers to the direction of the user, when the user has the handle in her hand, and "distal" refers to the direction away from the user and towards the patient, in the same situation. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

I claim:

1. A handle positioned at a proximal end of a catheter for delivering, from a distal end of the catheter, a stent positioned within a sheath, the handle comprising:
    an upper rack fixed to the handle;
    an upper distal block moveable along the upper rack and defining a pawl configured to permit only proximal movement in relation to the upper rack;
    an upper proximal block moveable along the upper rack and defining a pawl configured to permit only proximal movement in relation to the upper rack;
    a lower rack configured to slide proximally and, alternatingly, distally in relation to the handle;
    a lower distal block moveable along the lower rack and defining a pawl configured to permit only proximal movement in relation to the lower rack;
    a lower proximal block moveable along the lower rack and defining a pawl configured to permit only proximal movement in relation to the lower rack;
    wherein, the upper distal block is operably connected to a proximal end of a sheath actuator, a distal end of the sheath actuator being operably connected to the sheath;
    wherein, the lower proximal block is operably connected to a proximal end of a stent actuator, a distal end of the stent actuator being operably connected to a stent engagement member.

2. The handle of claim 1, further including:
    a beam;
    an upper distal link connected at a first end to the upper distal block and at a second end to the beam;
    an upper proximal link connected at a first end to the upper proximal block and at a second end to the beam;
    a lower distal link connected at a first end to the lower distal block and at a second end to the beam; and
    a lower proximal link connected at a first end to the lower proximal block and at a second end to the beam.

3. The handle of claim 1, further including:
    an additional rack configured to move in conjunction with the lower rack;
    a shuttle that surrounds the lower proximal block so as to move in conjunction with the lower proximal block, the shuttle including an arm that ends in a second pawl;
    wherein the additional rack is configured to permit movement of the second pawl on the arm only in a distal direction in relation to the lower rack.

4. The handle of claim 1, further including a trigger pivotingly connected to the handle and in communication with the lower rack, whereby activation of the trigger causes distal movement of the lower rack.

5. The handle of claim 1, further including a spring connected between the handle and the lower rack and configured to bias the lower rack in a proximal direction.

6. The handle of claim 1, wherein the sheath actuator is an elongate tube.

7. The handle of claim 1, wherein the stent actuator is an elongate cylinder.

8. The handle of claim 1, wherein the sheath actuator is an elongate tube and the stent actuator is an elongate cylinder sized to slide within a lumen of the sheath actuator.

9. The handle of claim 1, further including:
an additional rack formed in the handle;
an arm that ends in a third pawl, the arm extending from the upper distal block;
wherein the additional rack is configured to prevent proximal movement of the upper distal block when the third pawl is engaged with the additional rack.

* * * * *